US008542902B2

(12) United States Patent
Ohishi

(10) Patent No.: US 8,542,902 B2
(45) Date of Patent: Sep. 24, 2013

(54) X-RAY IMAGING APPARATUS

(75) Inventor: Satoru Ohishi, Otawara (JP)

(73) Assignees: Kabushiki Kaisha Toshiba, Tokyo (JP); Toshiba Medical Systems Corporation, Tochigi-Ken (JP)

( * ) Notice: Subject to any disclaimer, the term of this patent is extended or adjusted under 35 U.S.C. 154(b) by 290 days.

(21) Appl. No.: 12/911,906

(22) Filed: Oct. 26, 2010

(65) Prior Publication Data

US 2011/0103666 A1 May 5, 2011

(30) Foreign Application Priority Data

Oct. 29, 2009 (JP) ................................. 2009-249456
Sep. 30, 2010 (JP) ................................. 2010-222249

(51) Int. Cl.
*G06K 9/00* (2006.01)

(52) U.S. Cl.
USPC .......................................................... 382/131

(58) Field of Classification Search
None
See application file for complete search history.

(56) References Cited

U.S. PATENT DOCUMENTS

| 7,256,782 | B2 * | 8/2007 | Aoyama ....................... 345/426 |
| 2008/0097150 | A1 * | 4/2008 | Hasegawa et al. ............ 600/109 |
| 2009/0005679 | A1 * | 1/2009 | Dala-Krishna ................ 600/437 |
| 2009/0088830 | A1 * | 4/2009 | Mohamed et al. ............ 623/1.11 |
| 2010/0217116 | A1 * | 8/2010 | Eck et al. ...................... 600/424 |

FOREIGN PATENT DOCUMENTS

| CN | 101023872 A | 8/2007 |
| CN | 101028194 A | 9/2007 |
| JP | 2003-143479 A | 5/2003 |
| JP | 2007-229473 A | 9/2007 |

OTHER PUBLICATIONS

Stuart J. Hutchison (Dec. 10, 2008). Complications of Myocardial Infarction: Clinical Diagnostic Imaging Atlas. Elsevier Health Sciences. ISBN 978-1-4160-5272-2. http://books.google.com/books?id=yFQGgX643qQC. Retrieved Nov. 15, 2012.*
Frangi, Laura Dempere-Marco, Estanislao Oubel, Marcelo Castro, Christopher Putman, Alejandro, and Juan Cebral. "CFD Analysis Incorporating the Influence of Wall Motion: Application to Intracranial Aneurysms." SpringerLink. Springer Science Business Media, n.d. 2006 Web. Nov. 19, 2012. <http://www.springerlink.com/content/3757621n3034lt53/MUD=MP>.*
Weese, J.; Penney, G.P.; Desmedt, P.; Buzug, T.M.; Hill, D.L.G.; Hawkes, D.J.; , "Voxel-based 2-D/3-D registration of fluoroscopy images and CT scans for image-guided surgery," Information Technology in Biomedicine, IEEE Transactions on , vol. 1, No. 4, pp. 284-293, Dec. 1997 doi: 10.1109/4233.681173 URL: http://ieeexplore.ieee.org/stamp/stamp.jsp?tp=.*
Noboru Niki et al., "3D Diagnostic Imaging of Blood Vessels using an X-Ray Rotational Angiographic System", AAAI Technical Report SS-94-05, 1994.
Chinese Office Action for corresponding CN Application No. 201010530368.0 mailed on Jul. 4, 2012 and English summary.

* cited by examiner

*Primary Examiner* — Stephen R Koziol
*Assistant Examiner* — Amandeep Saini
(74) *Attorney, Agent, or Firm* — Yoshida & Associates, LLC

(57) ABSTRACT

In an X-ray imaging apparatus according to an embodiment, a three-dimensional blood-vessel image collecting unit collects a three-dimensional blood vessel image. An X-ray image collecting unit collects an X-ray image. A composite-image creating unit then creates a three-dimensional projection image projected based on a state of the X-ray imaging apparatus from the collected three-dimensional blood vessel image, and creates a composite image of the created three-dimensional projection image and the X-ray image. A displacement determining unit then determines a displacement between an aneurysm on the three-dimensional projection image and the aneurysm on the X-ray image. Subsequently, a registration unit registers the composite image by using the determined displacement, and displays the registered composite image onto a display unit.

20 Claims, 8 Drawing Sheets

ANEURYSM ON X-RAY FLUOROSCOPIC IMAGE

ANEURYSM ON VOLUME RENDERING IMAGE

PRESENT CENTER OF ANEURYSM (IN X-RAY FLUOROSCOPIC/ ACQUISITION IMAGE)

X-RAY DETECTOR

DISPLACEMENT

CENTER OF ANEURYSM ON THREE-DIMENSIONAL BLOOD VESSEL IMAGE

X-RAY TUBE

MOMENT OF COLLECTING
THREE-DIMENSIONAL
BLOOD VESSEL IMAGE

CATHETER

MOMENT OF 3D ROADMAP

AFTER REGISTRATION

AFTER REGISTRATION
(ENLARGED)

AFTER POSITIONAL AND
ANGULAR REGISTRATIONS

AFTER POSITIONAL AND
ANGULAR REGISTRATIONS
(ENLARGED)

MOMENT OF COLLECTING
THREE-DIMENSIONAL
BLOOD VESSEL IMAGE

MOMENT OF 3D ROADMAP

X-RAY IMAGING APPARATUS

CROSS-REFERENCE TO RELATED APPLICATIONS

This application is based upon and claims the benefit of priority from Japanese Patent Application No. 2009-249456, filed on Oct. 29, 2009; and Japanese Patent Application No. 2010-222249, filed on Sep. 30, 2010, the entire contents of all of which are incorporated herein by reference.

FIELD

Embodiments described herein relate generally to an X-ray imaging apparatus.

BACKGROUND

According to an intervention treatment, which is one of treatment methods for an aneurysm, a doctor carries out insertion of a catheter or a guide wire while watching an X-ray fluoroscopic image displayed on a monitor. However, it is difficult to confirm visually a blood vessel on an X-ray fluoroscopic image unless injecting contrast media. On the other hand, if continuously injecting contrast media, a burden onto a patient becomes high. For this reason, conventionally, a roadmap function of displaying a composite image of a past image taken by injecting contrast media and an X-ray fluoroscopic image in real time onto a monitor has been used.

However, such roadmap function cannot cope with a displacement arising along with a state change in the X-ray imaging apparatus (for example, a movement of a bed, or a rotation of an arm), consequently, an image taken by injecting contrast media needs to be re-created each time. Re-creation leads to an increase in the quantity of contrast media to be used, and results in a burden onto the patient. Therefore, recently, a three-dimensional (3D) roadmap function has come into use, which includes preliminarily collecting a three-dimensional blood vessel image on which a blood vessel image is enhanced, and during a treatment, creating a three-dimensional projection image (hereinafter, "volume rendering image") from the three-dimensional blood vessel image so as to reflect a state change in the X-ray imaging apparatus, and displaying a composite image of the created volume rendering image and an X-ray fluoroscopic image onto a monitor (for example, JP-A 2007-229473 (KOKAI)).

However, even if using the above 3D roadmap function, there is a problem that a displacement of an aneurysm arising along with insertion of a catheter or another tool cannot be coped with.

In other words, according to the 3D roadmap function, a volume rendering image is to be created from a preliminarily collected three-dimensional blood vessel image; however, the three-dimensional blood vessel image is collected in a state where catheter or other tool is not inserted (or is at a starting part of the blood vessel). On the other hand, for example, if a catheter is inserted up to the vicinity of an aneurysm, a bending force of the catheter along a blood vessel and a resilient force are generated, and the blood vessel deforms so as to reduce a bend of the blood vessel. Consequently, not only the position of the blood vessel, but also the position of the aneurysm is displaced from the position at the moment of collecting the three-dimensional blood-vessel image, resulting in that the position of the aneurysm is displayed on a monitor in a displaced state.

DETAILED DESCRIPTION

Exemplary embodiments of an X-ray imaging apparatus will be explained below in detail with reference to the accompanying drawings.

An X-ray imaging apparatus according to the embodiments includes a three-dimensional blood-vessel image collecting unit, an X-ray image collecting unit, a composite-image creating unit, a displacement determining unit, and a registration unit. The three-dimensional blood-vessel image collecting unit collects a three-dimensional blood vessel image on which a blood vessel image is enhanced. The X-ray image collecting unit collects an X-ray image. The composite-image creating unit creates a three-dimensional projection image projected based on a state of the X-ray imaging apparatus from a three-dimensional blood vessel image collected by the three-dimensional blood-vessel image collecting unit, and creates a composite image of the created three-dimensional projection image and the X-ray image collected by the X-ray image collecting unit. The displacement determining unit determines a displacement between an aneurysm on the three-dimensional projection image and the aneurysm on the X-ray image. The registration unit registers the composite image created by the composite-image creating unit by using the displacement determined by the displacement determining unit, and displays the registered composite image onto a display unit.

Figure 1:
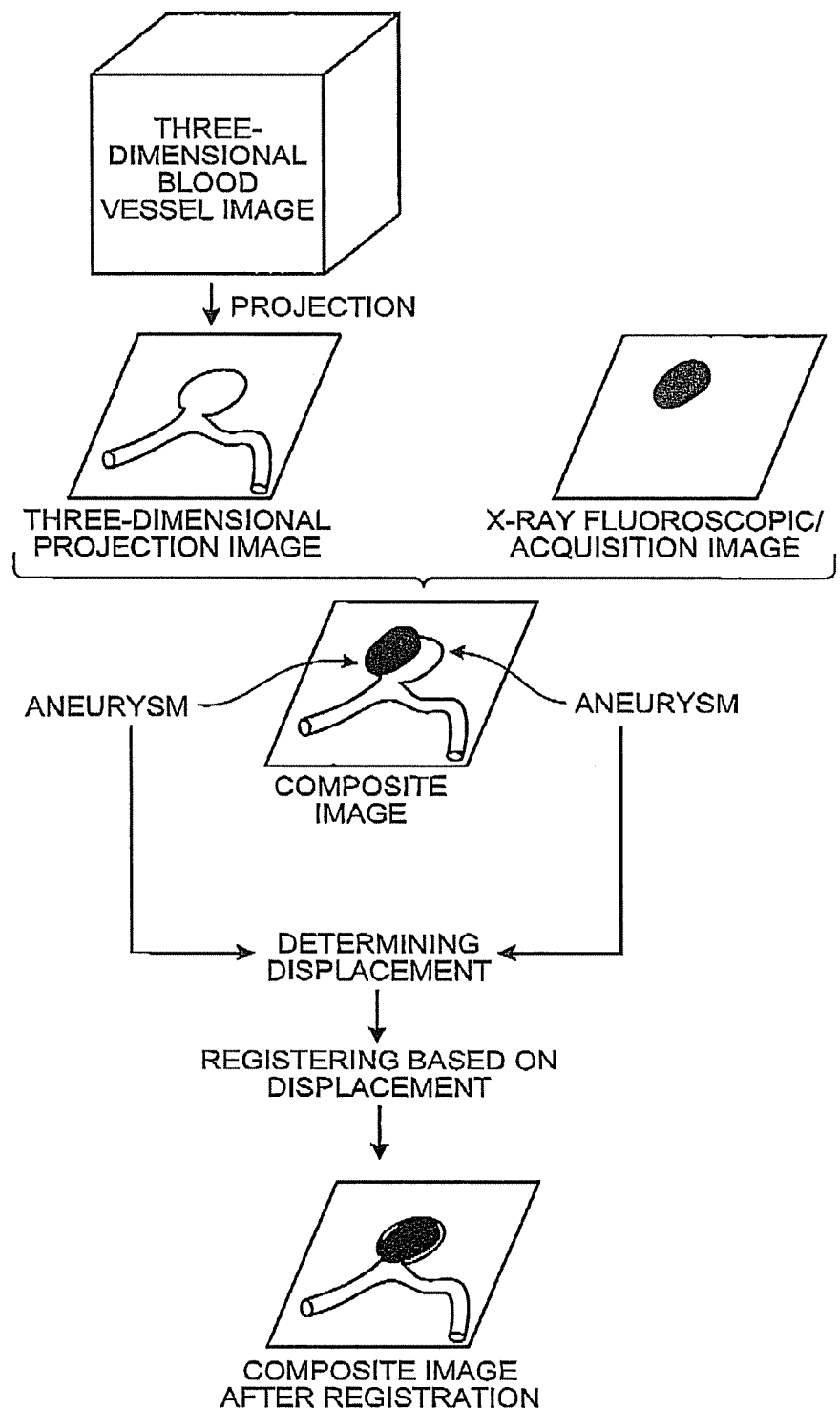
FIG. 1 is a schematic diagram for explaining an overview of an X-ray imaging apparatus according to a first embodiment.

First of all, an overview of an X-ray imaging apparatus according to a first embodiment is explained below with reference to FIG. 1. FIG. 1 is a schematic diagram for explaining an overview of the X-ray imaging apparatus according to the first embodiment.

As shown in FIG. 1, the X-ray imaging apparatus according to the first embodiment collects a three-dimensional blood vessel image on which a blood vessel image is enhanced. The X-ray imaging apparatus collects an X-ray fluoroscopic image.

The X-ray imaging apparatus then creates a three-dimensional projection image projected based on a state of the X-ray imaging apparatus from the collected three-dimensional blood vessel image, and creates a composite image of the created three-dimensional projection image and the X-ray fluoroscopic image.

Subsequently, the X-ray imaging apparatus determines a displacement between an aneurysm on the three-dimensional projection image and the aneurysm on the X-ray fluoroscopic image from the created composite image.

The X-ray imaging apparatus then registers the composite image based on the determined displacement, and displays the registered composite image onto a display unit.

In this way, the X-ray imaging apparatus according to the first embodiment registers the three-dimensional projection image and the X-ray fluoroscopic image based on information about the aneurysm that is an observation portion. As a result, the displacement of the aneurysm on the composite image can be registered, so that the position of the aneurysm on the three-dimensional projection image and the position of the aneurysm on the X-ray fluoroscopic image are matched with each other on the composite image. For example, according to a conventional three-dimensional (3D) roadmap function, a displacement of an aneurysm brings about difficulty in comparing total shapes of the aneurysm, thereby resulting in a situation that it is difficult to grasp loading of a coil; however, according to the X-ray imaging apparatus of the first embodiment can avoid such situation.

Figure 2:
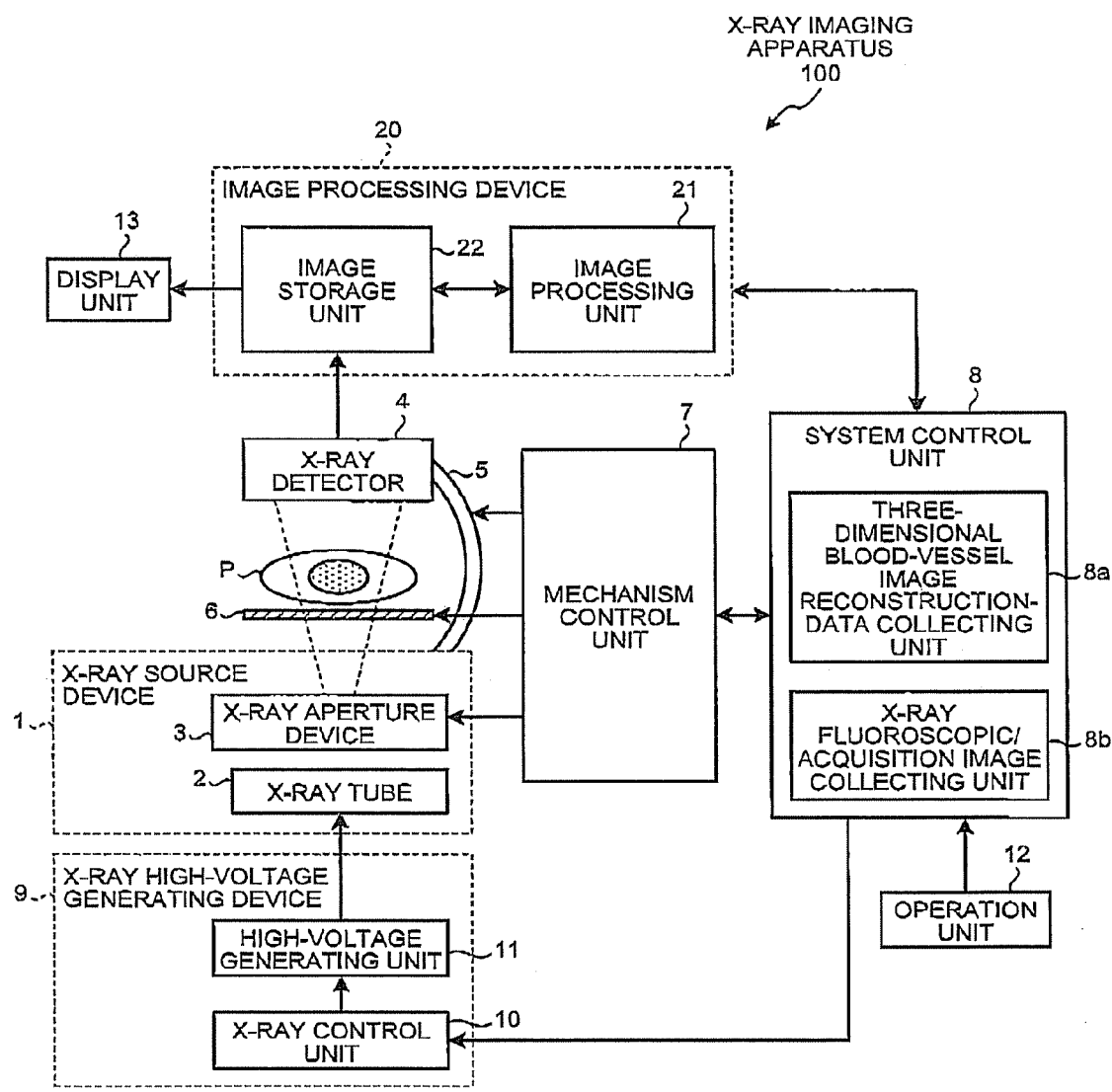
FIG. 2 is a functional block diagram of a configuration of the X-ray imaging apparatus according to the first embodiment.

A configuration of the X-ray imaging apparatus according to the first embodiment is explained below with reference to FIGS. 2 and 3. FIG. 2 is a functional block diagram of a configuration of the X-ray imaging apparatus according to the first embodiment.

As shown in FIG. 2, an X-ray imaging apparatus 100 according to the first embodiment includes an X-ray source device 1, an X-ray detector 4, an arm 5, a couch 6, a mechanism control unit 7, a system control unit 8, an X-ray high-voltage generating device 9, an operation unit 12, a display unit 13, and an image processing device 20.

The X-ray source device 1 includes an X-ray tube 2, and an X-ray aperture device 3. The X-ray tube 2 generates an X-ray by using a high voltage supplied by the X-ray high-voltage generating device 9. The X-ray aperture device 3 controls a radiation field by blocking part of an X-ray generated by the X-ray tube 2.

The X-ray detector 4 detects an X-ray having passed through a patient P by converting it into an electric charge.

The arm 5 supports the X-ray source device 1 and the X-ray detector 4. The arm 5 in a C shape rotates around the patient P at high speed as like a propeller with a motor provided on a base. The couch 6 is configured for the patient P to lie on. The mechanism control unit 7 controls rotation of the arm 5 and movement of the couch 6.

The system control unit 8 controls the whole of the X-ray imaging apparatus 100, and includes a three-dimensional blood-vessel image reconstruction-data collecting unit 8a, and an X-ray fluoroscopic/acquisition image collecting unit 8b. The three-dimensional blood-vessel image reconstruction-data collecting unit 8a controls the whole of the X-ray imaging apparatus 100 so as to collect data for reconstructing a three-dimensional blood vessel image in accordance with, such as an operation by an operator received by the operation unit 12, and stores the collected data into an image storage unit 22. The X-ray fluoroscopic/acquisition image collecting unit 8b controls the whole of the X-ray imaging apparatus 100 so as to collect an X-ray fluoroscopic image or an X-ray acquisition image in accordance with, such as an operation by the operator received by the operation unit 12, and stores the collected X-ray fluoroscopic image or the collected X-ray acquisition image into the image storage unit 22.

The X-ray high-voltage generating device 9 includes an X-ray control unit 10, and a high-voltage generating unit 11. The X-ray control unit 10 controls an X-ray generated by the X-ray tube 2 by controlling the high-voltage generating unit 11. The high-voltage generating unit 11 generates a high voltage to be supplied to the X-ray tube 2.

The operation unit 12 receives an operation by the operator to the X-ray imaging apparatus 100. The display unit 13 displays an image processed by the image processing device 20.

The image processing device 20 includes an image processing unit 21 and the image storage unit 22. The image processing unit 21 performs image processing on data detected by the X-ray detector 4 and stored by the image storage unit 22. The image storage unit 22 stores data detected by the X-ray detector 4, and an image processed by the image processing unit 21.

The image processing device 20 is further explained below with reference to FIG. 3. FIG. 3 is a functional block diagram of a configuration of the image processing unit.

Figure 3:
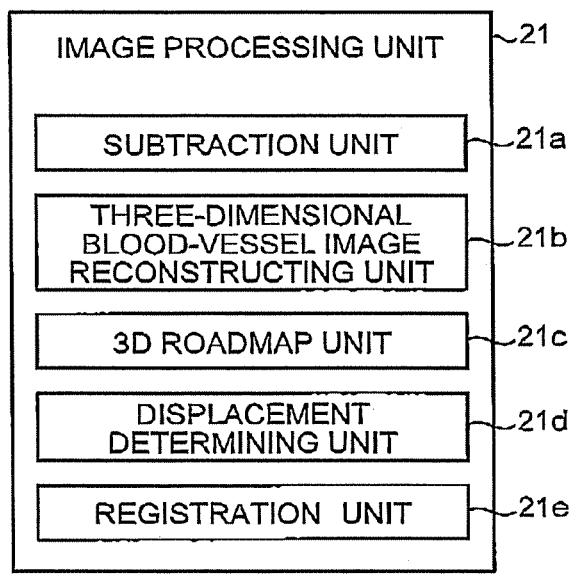
FIG. 3 is a functional block diagram of a configuration of an image processing unit shown in FIG. 2.

As shown in FIG. 3, the image processing unit 21 includes a subtraction unit 21a, a three-dimensional blood-vessel image reconstructing unit 21b, a 3D roadmap unit 21c, a displacement determining unit 21d, and an registration unit 21e.

The subtraction unit 21a performs subtraction processing by using data stored in the image storage unit 22, and creates a Digital Subtraction Angiography (DSA) image.

The three-dimensional blood-vessel image reconstructing unit 21b creates a three-dimensional blood vessel image from the DSA image created by the subtraction unit 21a.

The 3D roadmap unit 21c creates a volume rendering image that is projected based on a state of the X-ray imaging apparatus 100, from the three-dimensional blood vessel image created by the three-dimensional blood-vessel image reconstructing unit 21b, and creates a 3D roadmap image that the created volume rendering image and an X-ray fluoroscopic image are combined.

The displacement determining unit 21d determines a displacement between an aneurysm on the three-dimensional blood vessel image and the aneurysm on the X-ray fluoroscopic image, from the 3D roadmap image created by the 3D roadmap unit 21c.

The registration unit 21e registers the 3D roadmap image by using the displacement determines by the displacement determining unit 21d.

Figure 4:
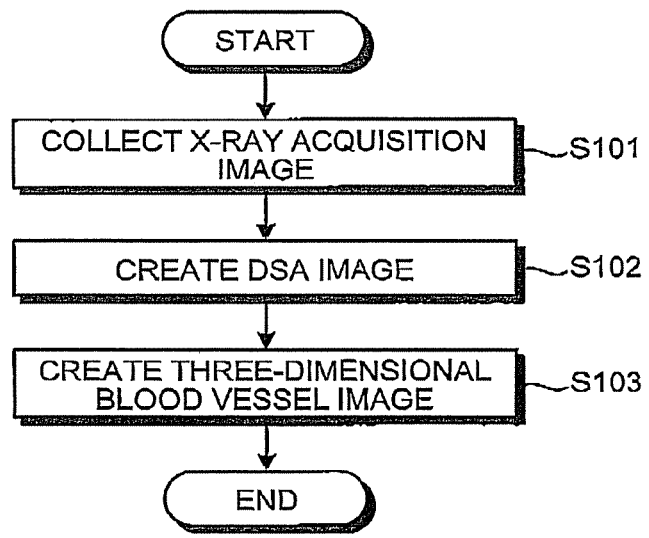
FIG. 4 is a flowchart for explaining three-dimensional (3D) blood-vessel image collecting processing.
Figure 5:
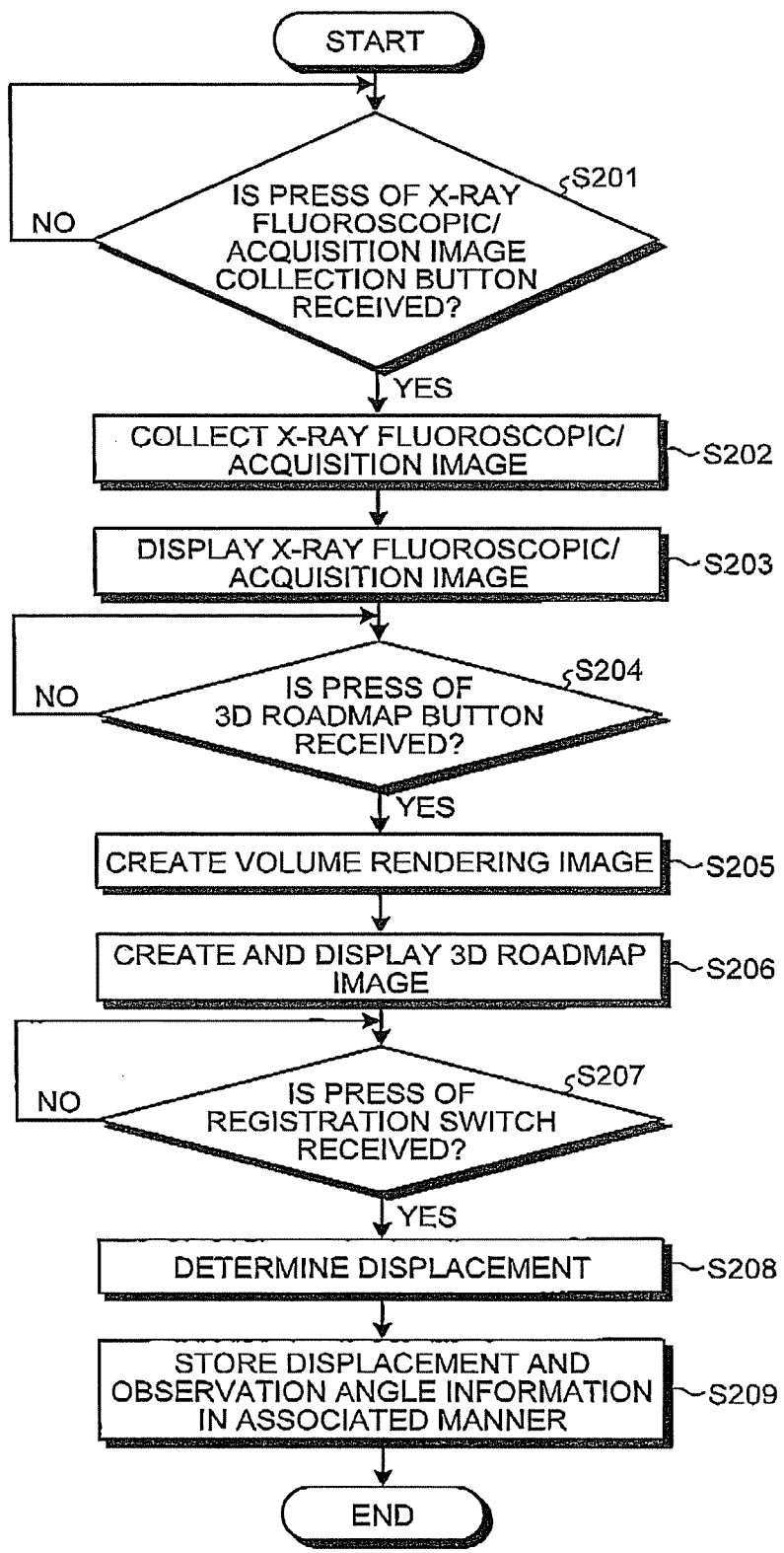
FIG. 5 is a flowchart for explaining 3D roadmap image registration processing.
Figure 6A:
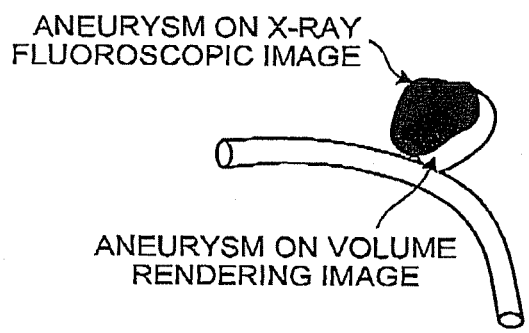
FIGS. 6A and 6B are schematic diagrams for explaining determination of a displacement.
Figure 6B:
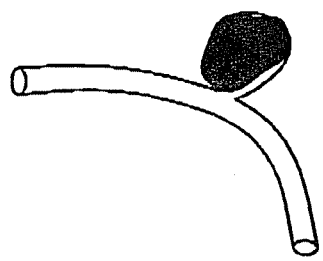
Figure 7A:
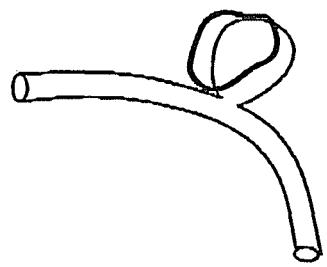
FIGS. 7A and 7B are schematic diagrams for explaining determination of a displacement.
Figure 7B:
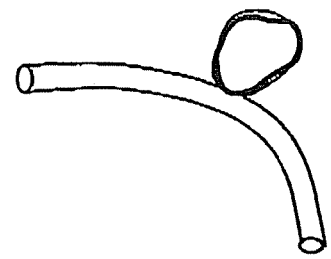
Figure 8:
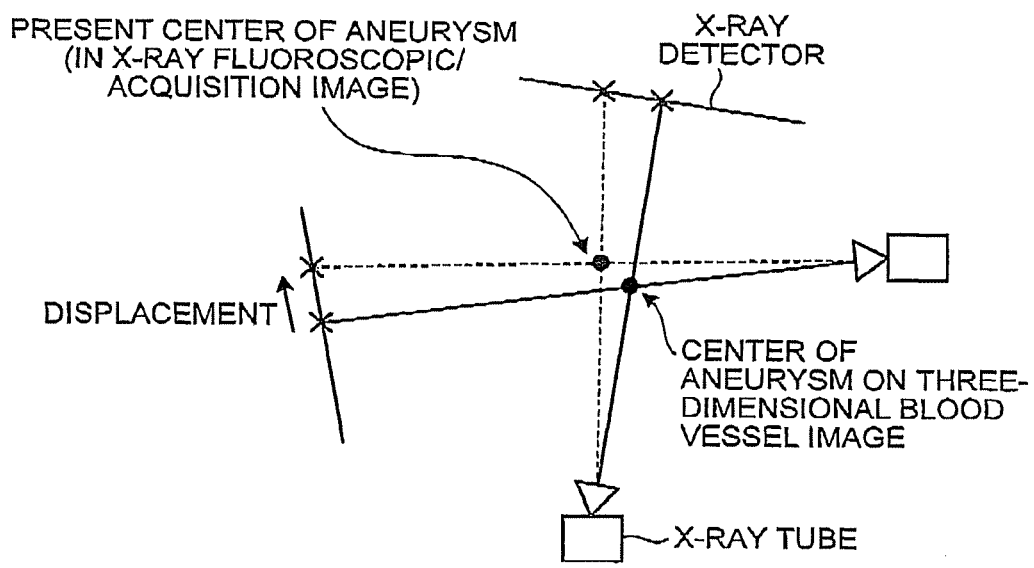
FIG. 8 is a schematic diagram for explaining determination from two directions.

A process procedure by the X-ray imaging apparatus according to the first embodiment is explained below with reference to FIGS. 4 to 6. FIG. 4 is a flowchart for explaining three-dimensional (3D) blood-vessel image collecting processing; and FIG. 5 is a flowchart for explaining 3D roadmap image registration processing. FIGS. 6A and 6B and FIGS. 7A and 7B are schematic diagrams for explaining determination of a displacement. FIG. 8 is a schematic diagram for explaining determination from two directions. The first embodiment assumes a case of performing an intervention treatment, which is one of treatment methods for an aneurysm.

To begin with, as a preliminary preparation for displaying a 3D roadmap image during a treatment, the X-ray imaging apparatus 100 according to the first embodiment collects a three-dimensional blood vessel image.

As shown in FIG. 4, under the operation by the operator, the three-dimensional blood-vessel image reconstruction-data collecting unit 8a of the system control unit 8 collects X-ray acquisition images for reconstructing a three-dimensional blood vessel image (Step S101).

Specifically, the operator adjusts one of the position of the couch 6, the height of the couch 6, and the position of the arm 5, or a combination of some of them, by operating the operation unit 12, so as to capture a main blood vessel to be a treatment target, in the field of view in all directions. The operator confirms afterward that, for example, rotation of the arm 5 poses no danger to the patient P, and then starts to take an X-ray acquisition image. The three-dimensional blood-vessel image reconstruction-data collecting unit 8a then starts to collect X-ray acquisition images.

Collection of X-ray acquisition images is performed twice, namely, before an injection of contrast media and after the injection. Before the injection of contrast media, while rotating the arm 5 at high speed as like a propeller by 50 degrees per second, the three-dimensional blood-vessel image reconstruction-data collecting unit 8a takes images, for example, at every two degrees, and collects 100 frames of X-ray acquisition images (Step S101). The collected 100 frames of the X-ray acquisition images are converted into digital signals by a not-shown analog-to-digital converter, and stored into the image storage unit 22. The three-dimensional blood-vessel image reconstruction-data collecting unit 8a returns the arm 5 to the initial rotation-starting position quickly.

Contrast media are then injected by a contrast-media injector into the patient P, and after a lapse of a certain time, the three-dimensional blood-vessel image reconstruction-data collecting unit 8a again takes images, for example, at every two degrees, while rotating the arm 5 at high speed as like a propeller by 50 degrees per second, and collects 100 frames of X-ray acquisition images. Similarly to the X-ray acquisition images collected before the injection of the contrast media, the collected 100 frames of the X-ray acquisition images are converted into digital signals by the not-shown analog-to-digital converter, and stored into the image storage unit 22.

Subsequently, the subtraction unit 21a of the image processing unit 21 creates a DSA image (Step S102).

Specifically, the subtraction unit 21a performs subtraction processing on X-ray acquisition images of corresponding angles by using the X-ray acquisition images before the injection of the contrast media and the X-ray acquisition images after the injection of the contrast media stored in the image storage unit 22 at Step S101, thereby creating a DSA image. The subtraction unit 21a then sends the created DSA image to the three-dimensional blood-vessel image reconstructing unit 21b.

The three-dimensional blood-vessel image reconstructing unit 21b of the image processing unit 21 then creates a three-dimensional blood vessel image (Step S103).

Specifically, the three-dimensional blood-vessel image reconstructing unit 21b reconstructs a three-dimensional volume image by using the DSA image sent from the subtraction unit 21a. As an example of reconstruction method, there are a Feldkamp method and ART (algebraic reconstruction technique). The former method is one of a filtered backprojection method, and latter method is one of iterative reconstruction method. The three-dimensional blood-vessel image reconstructing unit 21b for Feldkamp method performs appropriate convolution filtering processing, for example, Shepp & Logan, or Ramachandran, on the 100 frames of DSA images. The three-dimensional blood-vessel image reconstructing unit 21b then creates a three-dimensional blood vessel image by performing backprojection computing processing, and stores the created three-dimensional blood vessel image into the image storage unit 22.

A reconstruction region is defined as a cylinder that is inscribed in X-ray flux toward all directions of the X-ray tube. The inside of the cylinder needs to be three-dimensionally discreted at intervals of a length d in the center part of the reconstruction region to be projected to the width of one detecting element of the X-ray detector 4, and a reconstruction image of discrete points needs to be obtained. Although an example of discrete intervals is described here, other discrete intervals defined for the apparatus can be used.

In this way, collection of the three-dimensional blood vessel image as a preliminary preparation for displaying a 3D roadmap image during a treatment is finished.

When the preliminary preparation is finished, subsequently a treatment is started. In other words, insertion of a catheter by the operator, such as a doctor, is started. At that moment, as the catheter is inserted up to the vicinity of an aneurysm, a bending force of the catheter along a blood vessel and a resilient force are generated, and the blood vessel deforms so as to reduce a bend of the blood vessel. Consequently, not only the position of the blood vessel, but also the position of the aneurysm is displaced from the position at the moment of collecting the three-dimensional blood-vessel image.

When the catheter is inserted up to the vicinity of an aneurysm, the operator starts to collect two-dimensional projection data while injecting contrast media in order to grasp the position of the aneurysm accurately. In other words, as shown in FIG. 5 the X-ray imaging apparatus 100 receives a press of an X-ray acquisition image collection button (Yes at Step S201).

The X-ray imaging apparatus 100 then collects an X-ray acquisition image (Step S202). Specifically, the X-ray fluoroscopic/acquisition image collecting unit 8b of the system control unit 8 collects several frames before the injection of the contrast media, and a moving image to be collected at a certain rate after the injection of the contrast media, and stores the collected image data into the image storage unit 22. The subtraction unit 21a of the image processing unit 21 then creates a mask image by averaging the several frames before the injection of the contrast media stored in the image storage unit 22, and performs subtraction processing on the created mask image and the moving image after the injection of the contrast media with respect to each frame, thereby creating a DSA image.

The subtraction unit 21a then displays the created DSA image onto the display unit 13 (Step S203). The DSA image displayed on the display unit 13 is an image after the subtraction processing, on which a blood vessel image is enhanced.

The 3D roadmap unit 21c of the image processing unit 21 then determines whether a press of a 3D roadmap button is received, and waits until receiving the press (Step S204). At that moment, the final acquisition image of the DSA image is displayed on the display unit 13.

When the 3D roadmap unit 21c then determines that the 3D roadmap button is pressed as the operator presses the 3D roadmap button (Yes at Step S204), the 3D roadmap unit 21c creates a volume rendering image (Step S205).

Specifically, the 3D roadmap unit 21c reads a three-dimensional blood vessel image stored in the image storage unit 22, and creates a volume rendering image from the read three-dimensional blood vessel image. If there is a plurality of three-dimensional blood vessel images, for example, when a plurality of aneurysms is a treatment target, the 3D roadmap unit 21c displays the plurality of three-dimensional blood vessel images onto the display unit 13 in thumbnail, and receives selection by the operator.

The 3D roadmap unit 21c then receives information indicating a state of the X-ray imaging apparatus 100 from the system control unit 8, for example, an observation angle, an observation field of view, an observation magnification, and an observation position, and creates a volume rendering image so as to be matched with the state indicated by those information.

The 3D roadmap unit 21c then creates a 3D roadmap image, and displays it onto the display unit 13 (Step S206).

Specifically, the 3D roadmap unit 21c combines the volume rendering image created at Step S205 and the DSA image displayed on the display unit 13 at Step S203, and displays it onto the display unit 13.

Here, suppose a displacement occurs between the position of the aneurysm on the volume rendering image and the position of the aneurysm on the DSA image. For example, suppose a displacement shown in FIG. 6A occurs.

According to the first embodiment, when the displacement determining unit 21d of the image processing unit 21 receives a press of a registration switch (Yes at Step S207); the displacement determining unit 21d determines a displacement between the position of the aneurysm on the volume rendering image and the position of the aneurysm on the DSA image by using input afterward by the operator (Step S208).

For example, suppose after the operator presses a not-shown registration switch, the operator clicks the center of the aneurysm on the volume rendering image displayed on the display unit 13 by using an input device, such as a mouse, moves the volume rendering image through a drag operation so as to match the position of the aneurysm on the volume rendering image with the position of the aneurysm on the DSA image, and then releases the registration switch where the displacement is corrected. For example, suppose it is released at a position as shown in FIG. 6B. The displacement determining unit 21d then determines a displacement by using the operation information by the operator.

Subsequently, the displacement determining unit 21d associates the determined displacement with observation angle information at this moment, and stores it into the image storage unit 22 (Step S209).

The X-ray imaging apparatus 100 according to the first embodiment then stores registration information with respect to the observation angles in two directions. In other words, by repeating processing at Steps S201 to S209 except Step S204, registration information with respect to the observation angles in two directions is stored.

For example, it is assumed that insertion of a coil by the operator, such as a doctor, is started. A coil inserted at first is called a first coil, which is inserted so as to wrap around an aneurysm with a basket. For this reason, the shape of the coil precisely expresses outer contours of the aneurysm, so that the position of the aneurysm can be determined without injecting contrast media.

The operator starts to collect an X-ray fluoroscopic image while inserting a coil in order to grasp the position of the aneurysm accurately. In other words, shown in FIG. 5, the X-ray imaging apparatus 100 receives a press of an X-ray fluoroscopic image collection button (Yes at Step S201); and collects an X-ray fluoroscopic image (Step S202).

At this moment, the 3D roadmap button is in a pressed state, and a 3D roadmap image that the volume rendering image and the X-ray fluoroscopic image are combined is displayed on the display unit 13.

Here, suppose the observation angle is changed. The 3D roadmap unit 21c then receives information indicating a state of the X-ray imaging apparatus 100 from the system control unit 8, for example, an observation angle, an observation field of view, an observation magnification, and an observation position, and creates a volume rendering image so as to be matched with the state indicated by those information.

By receiving a press of the X-ray fluoroscopic image collection button, the 3D roadmap unit 21c then creates a 3D roadmap image, and displays it onto the display unit 13 (Step S206).

Here, suppose a displacement occurs again between the position of the aneurysm on the volume rendering image and the position of the aneurysm (coil) on the X-ray fluoroscopic image. For example, suppose a displacement as shown in FIG. 7A occurs.

When the displacement determining unit 21d of the image processing unit 21 receives a press of the registration switch (Yes at Step S207); the displacement determining unit 21d determines again a displacement between the position of the aneurysm on the volume rendering image and the position of the coil on the X-ray fluoroscopic image by using input afterward by the operator (Step S208).

For example, suppose after the operator presses the not-shown registration switch, the operator clicks the center of the aneurysm on the volume rendering image displayed on the display unit 13 by using the input device, such as a mouse, moves the volume rendering image through a drag operation so as to match the position of the aneurysm on the volume rendering image with the coil on the X-ray fluoroscopic image, and then releases the registration switch where the displacement is corrected. For example, suppose it is released at a position as shown in FIG. 7B. The displacement determining unit 21d then determines a displacement by using the operation information by the operator.

Subsequently, the displacement determining unit 21d associates the determined displacement with observation angle information at this moment, and stores it into the image storage unit 22 (Step S209). In this way, the X-ray imaging apparatus 100 according to the first embodiment stores registration information with respect to the observation angles in two directions.

As shown in FIG. 8, the aneurysm center position on the three-dimensional blood vessel image can be determined from the aneurysm center coordinates in two directions, and the present aneurysm center position can be determined from the coordinates of the displacement destination; accordingly, registration information for registering with respect to the observation angles in the two directions can be collected. The position at the moment of collecting the three-dimensional blood vessel image and the present position of the aneurysm in the three-dimensional space can be determined, and subsequent displacements can be automated. In other words, as the aneurysm center position on the three-dimensional blood vessel image is corrected so as to match with the present aneurysm center position, when the observation angle is changed afterward, the X-ray imaging apparatus 100 according to the first embodiment can display the registered 3D roadmap image onto the display unit 13.

As described above, the X-ray imaging apparatus 100 according to the first embodiment creates a volume rendering image that is projected based on a state of the X-ray imaging apparatus 100, and creates a 3D roadmap image of the created volume rendering image and an X-ray fluoroscopic image. The X-ray imaging apparatus 100 determines a displacement between an aneurysm on the volume rendering image and the aneurysm on the X-ray fluoroscopic image. The X-ray imaging apparatus 100 then registers the 3D roadmap image by using the determined displacement, and displays the registered 3D roadmap image onto the display unit 13.

Accordingly, the X-ray imaging apparatus 100 according to the first embodiment can correct a displacement of an aneurysm. In other words, the X-ray imaging apparatus 100 according to the first embodiment registers the volume rendering image and the X-ray fluoroscopic image based on information about the aneurysm that is an observation portion.

As a result, the displacement of the aneurysm can be corrected, so that the position of the aneurysm on the volume rendering image and the position of the aneurysm on the X-ray fluoroscopic image are matched with each other on the 3D roadmap image. For example, according to the conventional 3D roadmap function, a displacement of the aneurysm brings about difficulty in comparing a total shape of an aneurysm, thereby resulting in a situation that it is difficult to grasp loading of a coil; however, according to the X-ray imaging apparatus 100 of the first embodiment can avoid such situation.

The X-ray imaging apparatus 100 according to the first embodiment can use a method of collecting X-ray images from observation angles in at least two directions, and determining the position of an aneurysm in a three-dimensional space by using the X-ray images collected from the observation angles in at least two directions. In such case, the X-ray imaging apparatus 100 determines the position of an aneurysm in the three-dimensional space also from the three-dimensional blood vessel image, thereby determining the position of the aneurysm in the three-dimensional space at the moment of collecting the three-dimensional blood vessel image and the present position of the aneurysm in the three-dimensional space. The X-ray imaging apparatus 100 then corrects the aneurysm center position on the three-dimensional blood vessel image so as to match with the present aneurysm center position, thereby automatically correcting displacement even when the observation angle is changed. In such case, registration of the 3D roadmap image can be automated by using already collected information.

A second embodiment is explained below. Although the first embodiment has explained above the method of correcting only positional displacement of an aneurysm, the second embodiment explains below a method of correcting the angle of an aneurysm. FIGS. 9A to 9D are schematic diagrams for explaining differences of areas of an aneurysm.

Figure 9A:
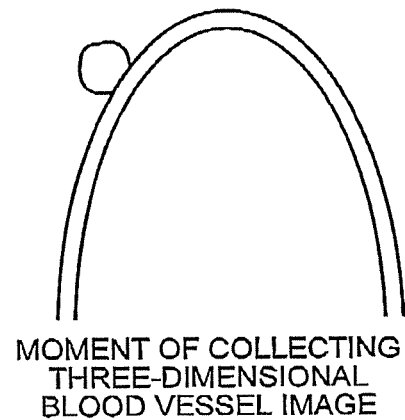
FIGS. 9A to 9D are schematic diagrams for explaining differences of areas of an aneurysm.
Figure 9B:
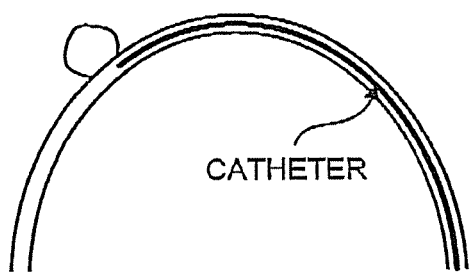

Sometimes, a position at which an aneurysm is produced is in a part with a large curvature, for example, as shown in FIG. 9A, in some cases. However, if a catheter is inserted up to the vicinity of the aneurysm for treating the aneurysm, the catheter tries to rebound to a straight line, so that the catheter deforms to a direction to have a smaller curvature as shown in FIG. 9B. As a result, a displacement occurs as described above.

Figure 9C:
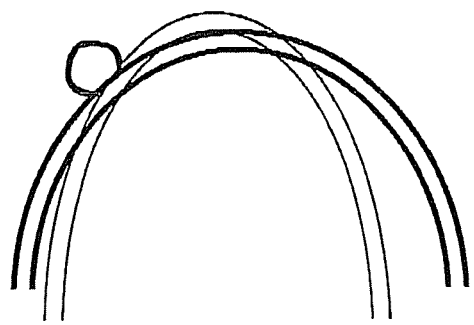
Figure 9D:
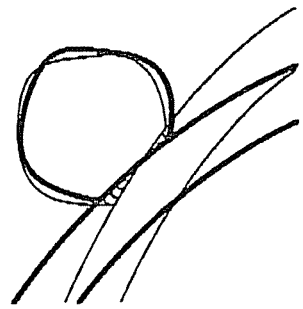

However, when change in the curvature is large, if only positional displacement is corrected, a difference still occurs in the area of the aneurysm, as shown in FIG. 9C. Specifically, an enlarged view of the aneurysm and its peripheral part are shown in FIG. 9D, in which shaded portions indicate differences in the area of the aneurysm between the moment of taking the three-dimensional blood vessel image and the moment of the 3D roadmap.

Figure 10A:
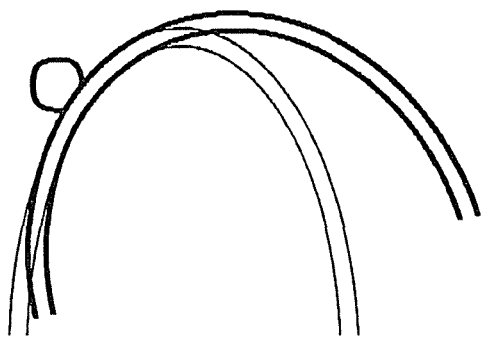
FIGS. 10A and 10B are schematic diagrams for explaining an area of an aneurysm after positional and angular registration.
Figure 10B:
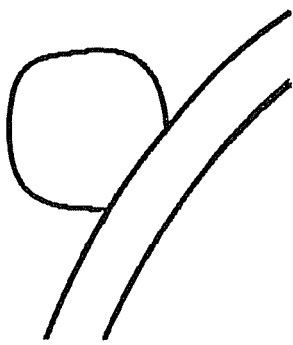

In order to correct the differences, the X-ray imaging apparatus 100 according to the second embodiment corrects not only the position of the aneurysm, but also the angle with a parent vessel, thereby being capable to match the area of the aneurysm completely between the moment of taking the three-dimensional blood vessel image and the moment of the 3D roadmap, as shown in FIGS. 10A and 10B. FIGS. 10A and 10B are schematic diagrams for explaining an area of an aneurysm after positional and angular registrations.

Figure 11A:
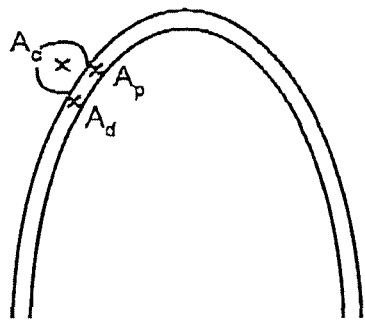
FIGS. 11A and 11B are schematic diagrams for explaining determination according to a second embodiment.
Figure 11B:
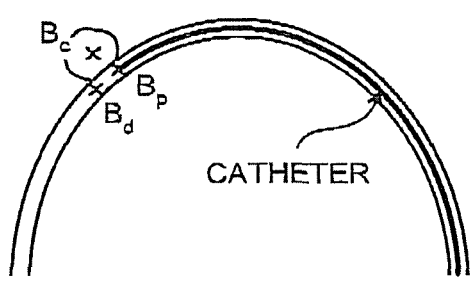

FIGS. 11A and 11B are schematic diagrams for explaining determination according to the second embodiment. For example, the displacement determining unit 21d of the image processing unit 21 determines the center of a parent vessel at proximal and distal positions of an aneurysm, as shown in FIGS. 11A and 11B. Here, it is assumed that the center of the aneurysm and the center positions of the parent vessel at proximal and distal positions of an aneurysm at the moment of taking the three-dimensional blood vessel image are denoted by $A_c$, $A_p$, and $A_d$, respectively. Furthermore, the center of the aneurysm and the center positions of the parent vessel in front and back of the aneurysm at the moment of 3D roadmap are denoted by $B_c$, $B_p$, and $B_d$, respectively.

The displacement determining unit 21d then registers the position and the angle so as to match $A_c$ and $B_c$, and so as to parallelize a straight line A connecting $A_p$ and $A_d$, and a straight line B connecting $B_p$ and $B_d$. The displacement determining unit 21d can directly determine three-dimensional coordinates of three points from the three-dimensional blood vessel image, can further determine three-dimensional coordinates by determining the present three points from two directions, and can automate positional and angular registrations afterward (in the third direction and afterward).

As described above, the X-ray imaging apparatus 100 according to the second embodiment determines the amount of inclination of a parent vessel in the vicinity of an aneurysm on a three-dimensional blood vessel image, and determines the amount of inclination of the parent vessel in the vicinity of the aneurysm on an X-ray image. The X-ray imaging apparatus 100 then registers a 3D roadmap image by using the determined displacement and the determined amount of inclination, and displays the registered 3D roadmap image onto the display unit 13.

Accordingly, the X-ray imaging apparatus 100 according to the second embodiment can correct an angular displacement of an aneurysm as well as a positional displacement. In other words, the X-ray imaging apparatus 100 according to the second embodiment corrects an angular displacement based on the amount of inclination of a parent vessel in the vicinity of the aneurysm. As a result, the angular displacement of the aneurysm can be corrected as veil as the positional displacement, so that the position of the aneurysm on the volume rendering image and the position of the aneurysm on the X-ray fluoroscopic image are more accurately matched with each other on the 3D roadmap image.

The X-ray imaging apparatus 100 according to the second embodiment can use a method of collecting X-ray images from observation angles in at least two directions, and determining the position of three points in the vicinity of an aneurysm in a three-dimensional space by using the X-ray images collected from the observation angles in at least two directions. In such case, the X-ray imaging apparatus 100 determines the position of the three points in the vicinity of the aneurysm in the three-dimensional space also from the three-dimensional blood vessel image, thereby determining the position of the three points in the vicinity of the aneurysm in the three-dimensional space at the moment of collecting the three-dimensional blood vessel image and the present position of the three points in the vicinity of the aneurysm in the three-dimensional space. The X-ray imaging apparatus 100 then registers the three-dimensional blood vessel image so as to match the aneurysm center position on the three-dimensional blood vessel image with the present aneurysm center position, and to match the parent vessel angle on the three-dimensional blood vessel image with the present parent vessel angle. Accordingly, even when the observation angle is changed, positional displacement and angular displacement can be automatically corrected.

Moreover, by combining it with the method of determining the position of the aneurysm in the three-dimensional space at the moment of collecting the three-dimensional blood vessel image and the present position of the aneurysm in the three-dimensional space, when the observation angle is changed afterward, the X-ray imaging apparatus 100 can automate registration of a 3D roadmap image against positional displacement and angular displacement by using already collected information.

Although the first embodiment and the second embodiment are explained above, an embodiment can be implemented by various different forms in addition to the embodiments described above.

Although the first embodiment explains above the method by which the X-ray imaging apparatus determines a displacement by using operation information by the operator (such as a drag operation), an embodiment is not limited to this. For example, it can be a method by which the operator is led to click the center of an aneurysm on a volume rendering image and to click the center of the aneurysm on an X-ray fluoroscopic image, and then a displacement is determined by using those operation information.

Moreover, for example, it can be a method by which the X-ray imaging apparatus determines an aneurysm by performing analysis processing on each of a volume rendering image and a DSA image/an X-ray fluoroscopic image, and determines displacement between aneurysms.

Various methods of analysis processing are conceivable. For example, a method can be used by which respective positions of the aneurysm on a volume rendering image and a DSA image are determined by continuously performing trace processing on boundaries between a blood vessel region and the other regions, detecting a discontinuous point during the trace processing, and determining that the point is a neck of the aneurysm, so that displacement is determined from the respective determined positions of the aneurysm.

Moreover, a method can be used by which the position of an aneurysm is determined from an X-ray fluoroscopic image by extracting the shape of a coil inserted into the aneurysm through threshold processing, and then displacement is determined by using the position of the aneurysm and a position of the aneurysm determined from a volume rendering image. A material having a high X-ray absorption coefficient, such as platinum, is used in a coil in the greater number of cases. Therefore, it can be configured to extract a coil through image processing in accordance with a threshold, and to determine that a portion extracted as the most outer coil is the boundary of an aneurysm.

Furthermore, for example, a method of determining displacement by performing correlation computing processing between a volume rendering image and a DSA image/an X-ray fluoroscopic image can be used.

It is specifically explained below. Between a volume rendering image and an X-ray fluoroscopic image, the displacement determining unit 21d performs correlation computing processing expressed by Expression (1) as follows:

$$\text{Error}(\Delta x, \Delta y) = \iint \{\text{Fluoro}(x-\Delta x, y-\Delta y) - RM(x,y)\}^2 dx\, dy \quad (1)$$

where, "$\Delta x$" denotes a displacement in the x axis direction between an aneurysm on the volume rendering image and the aneurysm on the X-ray fluoroscopic image. Moreover, "$\Delta y$" denotes a displacement in the y axis direction between the aneurysm on the volume rendering image and the aneurysm on the X-ray fluoroscopic image.

Furthermore, "Fluoro" stands for "fluorography", and corresponds to the X-ray fluoroscopic image in this case. Moreover, "RM" stands for "Roadmap", and corresponds to the volume rendering image on a 3D roadmap image in this case.

In other words, the right side of Expression (1) is a subtraction between the X-ray fluoroscopic image that is moved by "$\Delta x$" in the x axis direction and by "$\Delta y$" in the y axis direction, and the volume rendering image on the 3D roadmap image, so that as the higher the degree of matching between the both images becomes, the smaller the value of the left side, "Error($\Delta x, \Delta y$)", turns.

Therefore, the displacement determining unit 21d obtains "$\Delta x$" and "$\Delta y$" that bring "Error($\Delta x, \Delta y$)" to the minimum value by calculating.

The registration unit 21e then registers the 3D roadmap image in accordance with "$\Delta x$" and "$\Delta y$" calculated by the displacement determining unit 21d as registration information. For example, the registration unit 21e moves the position of the volume rendering image to be combined to the 3D roadmap image by "$\Delta x$" in the x axis direction and by "$\Delta y$" in the y axis direction, and combines anew the moved volume rendering image with the X-ray fluoroscopic image, thereby registering the 3D roadmap image.

When performing the correlation computing processing, a method can be used according to which the farther it is from the position of an aneurysm, the smaller weight is assigned to the correlation coefficient. In other words, suppose an aneurysm is relatively small in relation to the size of a blood vessel. Consequently, if only the correlation computing processing between the images is simply performed, there is a possibility that when a displacement of the blood vessel is corrected, it may be determined that "the displacement of the aneurysm is corrected". However, if the correlation coefficient is assigned with a weight, for example, the position of an aneurysm is determined from one of the images, and the farther it is from the position of the determined aneurysm, the smaller correlation coefficient is applied; registration by placing emphasis on displacement of the aneurysm can be performed in the correlation computing processing.

It is specifically explained below. Between a volume rendering image and an X-ray fluoroscopic image, the displacement determining unit 21d performs correlation computing processing expressed by Expression (2) as follows:

$$\text{Error}(\Delta x, \Delta y) = \qquad (2)$$
$$\iint \frac{1}{r+1}\{\text{Fluoro}(x-\Delta x, y-\Delta y) - RM(x,y)\}^2 dx, dy$$

in addition, $$r = \text{sqrt}\{(x-x_0)^2 + (y-y_0)^2\} \qquad (3)$$

It is assumed that "$x_0$" and "$y_0$" denote coordinates indicating the position of the aneurysm (for example, the center of the aneurysm) on the volume rendering image before registration. Consequently, "r" in Expression (3) denotes a distance from the position of the aneurysm (for example, the center of the aneurysm).

In other words, Expression (2) is an expression that Expression (1) is multiplied by "1/r+1" such that the farther it is from the position of the aneurysm, the smaller weight is assigned to the correlation coefficient. For example, when it is close to the center of the aneurysm, the value of "r" is small, so that a result of the subtraction between the volume rendering image and the X-ray fluoroscopic image is calculated with a weight close to "1". By contrast, when it is far from the center of the aneurysm, the value of "r" is large, so that a result of the subtraction between the volume rendering image and the X-ray fluoroscopic image is calculated with a weight much less than "1".

Therefore, the displacement determining unit 21*d* obtains "Δx" and "Δy" that bring "Error(Δx, Δy)" to the minimum value by calculating, according to Expression (2). The registration unit 21*e* then registers the 3D roadmap image in accordance with "Δx" and "Δy" calculated by the displacement determining unit 21*d* as registration information.

The method of determining displacement by performing correlation computing processing can be combined with the trace processing or the threshold processing described above. In other words, the correlation computing processing performed by the displacement determining unit 21*d* can be processing to be performed on a volume rendering image itself and an X-ray fluoroscopic image itself, or can be correlation computing processing to be performed between aneurysms extracted from respective images through the trace processing or the threshold processing.

The second embodiment explains above the example of performing registration of angular displacement in addition to positional displacement by determining the amount of inclination of a parent vessel in the vicinity of an aneurysm, and furthermore, correlation computing processing can be used for the registration.

It is specifically explained below. Between a volume rendering image and an X-ray fluoroscopic image, the displacement determining unit 21*d* performs correlation computing processing expressed by Expression (4) as follows:

$$\text{Error}(\Delta x, \Delta y, \Delta \theta) = \iint \{\text{Fluoro}(X - \Delta X_0, Y - \Delta Y_0) - \text{RM}(x,y)\}^2 dx\,dy \quad (4)$$

where, $$X = x \cos\theta - y \sin\theta \quad (5)$$

$$Y = x \sin\theta + y \cos\theta \quad (6)$$

$$\Delta X_0 = \Delta x \cos\theta - \Delta y \sin\theta \quad (7)$$

$$\Delta Y_0 = \Delta x \sin\theta + \Delta y \cos\theta \quad (8)$$

Precisely, "Δθ" denotes a rotational angle between an aneurysm on the volume rendering image and the aneurysm on the X-ray fluoroscopic image. Moreover, "X", "Y", "$\Delta X_0$", and "$\Delta Y_0$" are expressed by Expressions (5) to (8) described above. In this way, Expressions (4) to (8) express that the x coordinate and the y coordinate (the coordinate system of the x axis and the y axis) are converted into the coordinate system of the X axis and the Y axis, which the x axis and the y axis are rotated by θ degree, respectively; so that as the higher the degree of matching between the volume rendering image and the X-ray fluoroscopic image becomes, the smaller the value of the left side of Expression (4), "Error (Δx, Δy, Δθ)", turns.

Therefore, the displacement determining unit 21*d* obtains "Δx", "Δy", and "Δθ" that bring "Error(Δx, Δy, Δθ)" to the minimum value by calculating.

The registration unit 21*e* then registers the 3D roadmap image in accordance with "Δx", "Δy", and "Δθ" calculated by the displacement determining unit 21*d* as registration information. For example, the registration unit 21*e* moves the position of the volume rendering image to be combined to the 3D roadmap image by "Δx" in the x axis direction and by "Δy" in the y axis direction, and rotates it by "−Δθ", then combines anew the moved and rotated volume rendering image with the X-ray fluoroscopic image, thereby registering the 3D roadmap image.

Moreover, for example, a method of determining three-dimensional coordinates indicating the center of an aneurysm by performing ray trace processing on the aneurysm on a volume rendering image can be used. Furthermore, for example, a method of determining an aneurysm and determining a displacement by performing image processing of detecting a round shape from each of a volume rendering image and an X-ray fluoroscopic image can be used.

Figure 12:
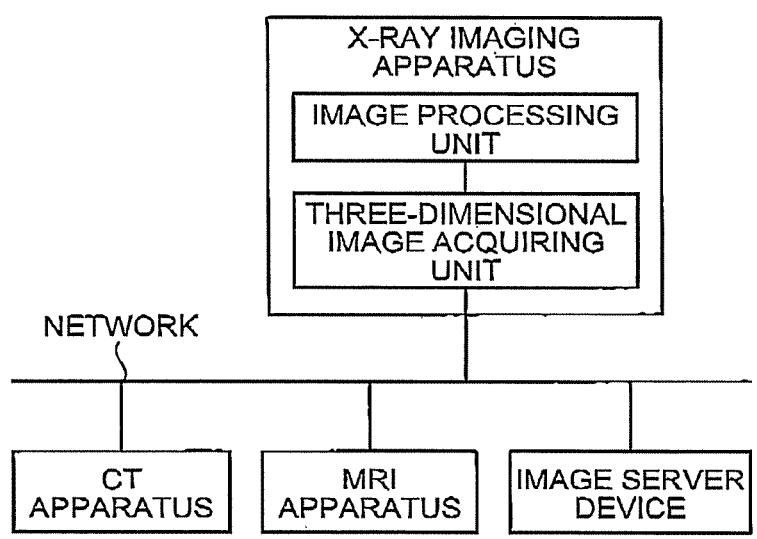
FIG. 12 is a schematic diagram for explaining a three-dimensional image acquiring unit.

Although the first embodiment explains above the method of using a three-dimensional blood vessel image that is created based on two-dimensional projection data collected by the X-ray imaging apparatus as a three-dimensional blood vessel image, an embodiment is not limited to this. For example, image data of Computed Tomography Angiography (CTA), Magnetic Resonance Angiography (MRA), no-contrast enhancement Magnetic Resonance Imaging (MRI), or the like, can be used. In such case, as shown in FIG. 12, the X-ray imaging apparatus can include a three-dimensional image acquiring unit, and the three-dimensional image acquiring unit can acquire those image data from another device via a network, for example, Ethernet (registered trademark). When the image data include human body information other than blood vessel information, blood vessel information can be additionally extracted by using a method of threshold processing, a method of specifying the range of pixel value, or a method of region growing, or a combination of some of them, and a three-dimensional blood vessel image can be created.

Moreover, the methods described above are not limited to the 3D roadmap function, and can be applied to a two-dimensional roadmap.

The first embodiment and the second embodiment explain above the methods according to which the X-ray imaging apparatus 100 uses as an X-ray image an X-ray acquisition image (DSA image) that is taken while injecting contrast media in the first time direction, and uses an X-ray fluoroscopic image in the second time direction. However, an embodiment is not limited to this. For example, it can be a method of using an X-ray fluoroscopic image that is taken while injecting contrast media in the first time direction, or a method of using an X-ray acquisition image in the second time direction. In other words, which of an X-ray acquisition image and an X-ray fluoroscopic image to be used as an X-ray image, and in what way to combine them to use are arbitrarily selectable. In the above description, "X-ray fluoroscopic image" is used as the meaning of an X-ray image that is taken with, for example, X-rays of a low radiation dose; on the other hand, "X-ray acquisition image" is used as the meaning of an X-ray image that is taken with, for example, X-rays of a high radiation dose.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray imaging apparatus comprising:
a three-dimensional blood-vessel image collecting unit that collects a three-dimensional blood vessel image on which a blood vessel image is enhanced;
an X-ray image collecting unit that collects an X-ray image;
a composite-image creating unit connected to the three-dimensional blood-vessel image collecting unit and the X-ray image collecting unit for creates creating a three-dimensional projection image projected based on a state of the X-ray imaging apparatus from the three-dimensional blood vessel image collected by the three-dimensional blood-vessel image collecting unit, and creates creating a composite image of created three-dimensional projection image and the X-ray image collected by the X-ray image collecting unit;
a displacement determining unit connected to the three-dimensional blood-vessel image collecting unit and the X-ray image collecting unit for determining a displacement caused by inserting an instrument up to the vicinity of an aneurysm between an aneurysm on the three-dimensional projection image and an aneurysm on the X-ray image; and
a registration unit connected to the three-dimensional blood-vessel image collecting unit, the X-ray image collecting unit, the composite-image creating unit and the displacement determining unit for correcting the aneurysm position on the three-dimensional blood vessel image by using the displacement determined by the displacement determining unit to generate a corrected three-dimensional blood vessel image so as to match with a position of the aneurysm on the X-ray image, and wherein the composite-image creating unit creates a corrected composite image using the corrected three-dimensional blood vessel image and the X-ray image and displays the corrected composite image onto a display unit.

2. The X-ray imaging apparatus according to claim 1, wherein the displacement determining unit determines respective positions of aneurysms on the three-dimensional projection image and the X-ray image, by continuously performing trace processing on a boundary between a blood-vessel region and a region other than the blood-vessel region, detecting a discontinuous point during the trace processing, and determining that the discontinuous point is a neck part of the aneurysm, thereby determining a displacement from respective determined positions of the aneurysms.

3. The X-ray imaging apparatus according to claim 1, wherein the displacement determining unit determines a position of the aneurysm from the X-ray image by extracting a shape of a coil inserted into the aneurysm through threshold processing, and determines a displacement by using determined position of the aneurysm and a position of the aneurysm determined from the three-dimensional projection image.

4. The X-ray imaging apparatus according to claim 1, wherein the displacement determining unit determines a displacement by performing correlation computing processing between the three-dimensional projection image and the X-ray image.

5. The X-ray imaging apparatus according to claim 2, wherein the displacement determining unit determines a displacement by performing correlation computing processing between the three-dimensional projection image and the X-ray image.

6. The X-ray imaging apparatus according to claim 3, wherein the displacement determining unit determines a displacement by performing correlation computing processing between the three-dimensional projection image and the X-ray image.

7. The X-ray imaging apparatus according to claim 4, wherein when performing the correlation computing processing, farther a position is from a position of an aneurysm, a smaller weight the displacement determining unit assigns to a correlation coefficient.

8. The X-ray imaging apparatus according to claim 5, wherein when performing the correlation computing processing, farther a position is from a position of an aneurysm, a smaller weight the displacement determining unit assigns to a correlation coefficient.

9. The X-ray imaging apparatus according to claim 6, wherein when performing the correlation computing processing, farther a position is from a position of an aneurysm, a smaller weight the displacement determining unit assigns to a correlation coefficient.

10. The X-ray imaging apparatus according to claim 1, wherein
the X-ray image collecting unit collects X-ray images from observation angles in at least two directions,
the displacement determining unit further includes
a first three-dimensional aneurysm-position determining unit that determines a position of the aneurysm in a three-dimensional space from the three-dimensional blood vessel image collected by the three-dimensional blood-vessel image collecting unit, and
a second three-dimensional aneurysm-position determining unit connected to the first three-dimensional aneurysm-position determining unit for determining a position of the aneurysm in a three-dimensional space by using X-ray images collected by the X-ray image collecting unit from observation angles in at least two directions, and
after positions of the aneurysm in the three-dimensional space are determined by the first three-dimensional aneurysm-position determining unit and the second three-dimensional aneurysm-position determining unit, the registration unit corrects the composite image so as to match both of determined positions in the three-dimensional space.

11. The X-ray imaging apparatus according to claim 4, wherein
the X-ray image collecting unit collects X-ray images from observation angles in at least two directions,
the displacement determining unit further includes
a first three-dimensional aneurysm-position determining unit that determines a position of the aneurysm in a three-dimensional space from the three-dimensional blood vessel image collected by the three-dimensional blood-vessel image collecting unit, and
a second three-dimensional aneurysm-position determining unit connected to the first three-dimensional aneurysm-position determining unit for determining a position of the aneurysm in a three-dimensional space by using X-ray images collected by the X-ray image collecting unit from observation angles in at least two directions, and
after positions of the aneurysm in the three-dimensional space are determined by the first three-dimensional aneurysm-position determining unit and the second three-dimensional aneurysm-position determining unit, the registration unit corrects the composite image so as to match both of determined positions in the three-dimensional space.

12. The X-ray imaging apparatus according to claim 7, wherein
the X-ray image collecting unit collects X-ray images from observation angles in at least two directions,
the displacement determining unit further includes
a first three-dimensional aneurysm-position determining unit that determines a position of the aneurysm in a three-dimensional space from the three-dimensional blood vessel image collected by the three-dimensional blood-vessel image collecting unit, and
a second three-dimensional aneurysm-position determining unit connected to the first three-dimensional aneurysm-position determining unit for determining a position of the aneurysm in a three-dimensional space by using X-ray images collected by the X-ray image collecting unit from observation angles in at least two directions, and
after positions of the aneurysm in the three-dimensional space are determined by the first three-dimensional aneurysm-position determining unit and the second three-dimensional aneurysm-position determining unit, the registration unit corrects the composite image so as to match both of determined positions in the three-dimensional space.

13. The X-ray imaging apparatus according to claim 1, further comprising a parent-vessel inclination-amount determining unit connected to the three-dimensional blood-vessel image collecting unit, the X-ray image collecting unit and the composite-image creating unit for determining an amount of inclination of a parent vessel in a vicinity of the aneurysm on the three-dimensional blood vessel image collected by the three-dimensional blood-vessel image collecting unit, and determines an amount of inclination of a parent vessel in a vicinity of the aneurysm on the X-ray image collected by the X-ray image collecting unit, wherein the registration unit corrects the composite image created by the composite-image creating unit by using the displacement determined by the displacement determining unit and the amount of the inclination determined by the parent-vessel inclination-amount determining unit, and displays the corrected composite image onto the display unit.

14. The X-ray imaging apparatus according to claim 2, further comprising a parent-vessel inclination-amount determining unit connected to the three-dimensional blood-vessel image collecting unit, the X-ray image collecting unit and the composite-image creating unit for determining an amount of inclination of a parent vessel in a vicinity of the aneurysm on the three-dimensional blood vessel image collected by the three-dimensional blood-vessel image collecting unit, and determines an amount of inclination of a parent vessel in a vicinity of the aneurysm on the X-ray image collected by the X-ray image collecting unit, wherein the registration unit corrects the composite image created by the composite-image creating unit by using the displacement determined by the displacement determining unit and the amount of the inclination determined by the parent-vessel inclination-amount determining unit, and displays the corrected composite image onto the display unit.

15. The X-ray imaging apparatus according to claim 3, further comprising a parent-vessel inclination-amount determining unit connected to the three-dimensional blood-vessel image collecting unit, the X-ray image collecting unit and the composite-image creating unit for determining an amount of inclination of a parent vessel in a vicinity of the aneurysm on the three-dimensional blood vessel image collected by the three-dimensional blood-vessel image collecting unit, and determines an amount of inclination of a parent vessel in a vicinity of the aneurysm on the X-ray image collected by the X-ray image collecting unit, wherein the registration unit corrects the composite image created by the composite-image creating unit by using the displacement determined by the displacement determining unit and the amount of the inclination determined by the parent-vessel inclination-amount determining unit, and displays the corrected composite image onto the display unit.

16. The X-ray imaging apparatus according to claim 4, further comprising a parent-vessel inclination-amount determining unit connected to the three-dimensional blood-vessel image collecting unit, the X-ray image collecting unit and the composite-image creating unit for determining an amount of inclination of a parent vessel in a vicinity of the aneurysm on the three-dimensional blood vessel image collected by the three-dimensional blood-vessel image collecting unit, and determines an amount of inclination of a parent vessel in a vicinity of the aneurysm on the X-ray image collected by the X-ray image collecting unit, wherein the registration unit corrects the composite image created by the composite-image creating unit by using the displacement determined by the displacement determining unit and the amount of the inclination determined by the parent-vessel inclination-amount determining unit, and displays the corrected composite image onto the display unit.

17. The X-ray imaging apparatus according to claim 10, further comprising a parent-vessel inclination-amount determining unit connected to the three-dimensional blood-vessel image collecting unit, the X-ray image collecting unit and the composite-image creating unit for determining an amount of inclination of a parent vessel in a vicinity of the aneurysm on the three-dimensional blood vessel image collected by the three-dimensional blood-vessel image collecting unit, and determines an amount of inclination of a parent vessel in a vicinity of the aneurysm on the X-ray image collected by the X-ray image collecting unit, wherein the registration unit corrects the composite image created by the composite-image creating unit by using the displacement determined by the displacement determining unit and the amount of the inclination determined by the parent-vessel inclination-amount determining unit, and displays the corrected composite image onto the display unit.

18. The X-ray imaging apparatus according to claim 13, wherein
the X-ray image collecting unit collects X-ray images from observation angles in at least two directions,
the displacement determining unit further includes
a first three-dimensional vicinity-point position determining unit that determines positions of certain points in a vicinity of the aneurysm in a three-dimensional space from the three-dimensional blood vessel image collected by the three-dimensional blood-vessel image collecting unit, and
a second three-dimensional vicinity-point position determining unit connected to the first three-dimensional aneurysm-position determining unit for determining positions of certain points in a vicinity of the aneurysm in a three-dimensional space by using X-ray images collected by the X-ray image collecting unit from observation angles in at least two directions, and
after positions of the certain points in the vicinity of the aneurysm in the three-dimensional space are determined by the first three-dimensional vicinity-point position determining unit and the second three-dimensional vicinity-point position determining unit, t-the registration unit corrects the composite image so as to match both of blood vessel angles of the parent vessel obtained from determined positions in the three-dimensional space.

19. The X-ray imaging apparatus according to claim 14, wherein the X-ray image collecting unit collects X-ray images from observation angles in at least two directions, the displacement determining unit further includes a first three-dimensional vicinity-point position determining unit that determines positions of certain points in a vicinity of the aneurysm in a three-dimensional space from the three-dimensional blood vessel image collected by the three-dimensional blood-vessel image collecting unit, and a second three-dimensional vicinity-point position determining unit connected to the first three-dimensional aneurysm-position determining unit for determining positions of certain points in a vicinity of the aneurysm in a three-dimensional space by using X-ray images collected by the X-ray image collecting unit from observation angles in at least two directions, and after positions of the certain points in the vicinity of the aneurysm in the three-dimensional space are determined by the first three-dimensional vicinity-point position determining unit and the second three-dimensional vicinity-point position determining unit, t-the registration unit corrects the composite image so as to match both of blood vessel angles of the parent vessel obtained from determined positions in the three-dimensional space.

20. The X-ray imaging apparatus according to claim 15, wherein the X-ray image collecting unit collects X-ray images from observation angles in at least two directions, the displacement determining unit further includes a first three-dimensional vicinity-point position determining unit that determines positions of certain points in a vicinity of the aneurysm in a three-dimensional space from the three-dimensional blood vessel image collected by the three-dimensional blood-vessel image collecting unit, and a second three-dimensional vicinity-point position determining unit connected to the first three-dimensional aneurysm-position determining unit for determining positions of certain points in a vicinity of the aneurysm in a three-dimensional space by using X-ray images collected by the X-ray image collecting unit from observation angles in at least two directions, and after positions of the certain points in the vicinity of the aneurysm in the three-dimensional space are determined by the first three-dimensional vicinity-point position determining unit and the second three-dimensional vicinity-point position determining unit, the registration unit corrects the composite image so as to match both of blood vessel angles of the parent vessel obtained from determined positions in the three-dimensional space.

* * * * *